Feb. 1, 1966 E. S. BOERNER Plant Pat. 2,594
ROSE PLANT
Filed Nov. 17, 1964
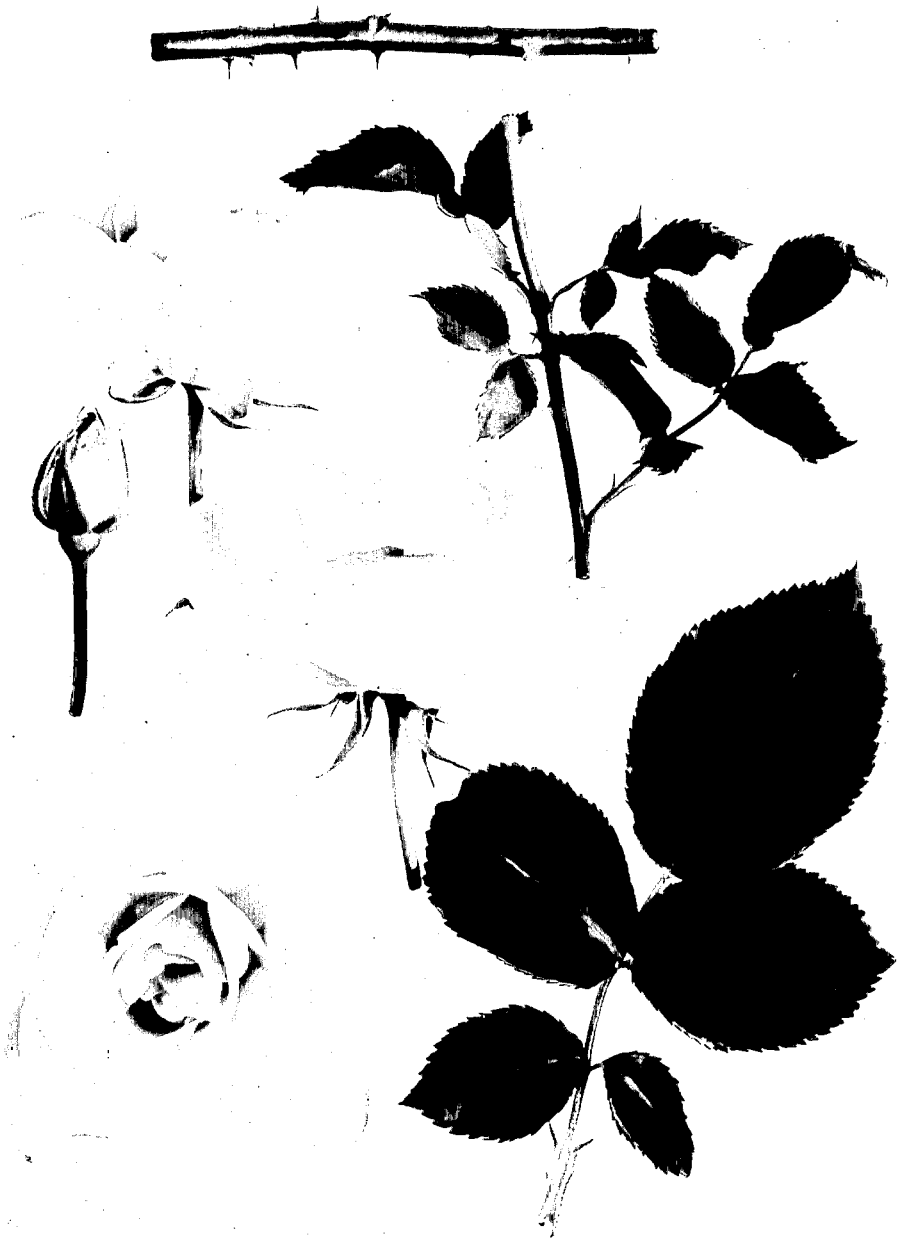
Inventor.
E. S. Boerner
By: Robb & Robb
Attorneys United States Patent Office Plant Pat. 2,594
Patented Feb. 1, 1966

2,594
ROSE PLANT

Eugene S. Boerner, Newark, N.Y., assignor to Jackson & Perkins Company, Newark, N.Y., a corporation of New York Filed Nov. 17, 1964, Ser. No. 411,953
1 Claim. (Cl. Plt.—22)

The present invention relates to a new and distinct variety of rose plant of the floribunda class, which was originated by me by crossing an unnamed seedling of unknown parentage with the variety known as "Spartan" (Plant Patent No. 1,357).

The primary objective of this breeding was to produce a new rose variety which bears flowers having a color range different from that of the parent variety "Spartan," while retaining the foliage characteristics of this parent variety. This objective was fully achieved along with other desirable improvements, as evidenced by the following unique combination of characteristics which are outstanding in the new variety and which distinguish it from its parents, as well as from all other varieties of which I am aware:

(1) Persistent foliage which reaches to the ground all summer long;

(2) A prolific flowering habit; and (3) A distinctive, attractive and unusual general color tonality of the flowers corresponding to Pale Yellow-Orange, with the upper half of the petals being lightly overcast with Orange-Pink, and with the lower half of the petals being overcast with Straw-Yellow.

Asexual reproduction of my new variety by budding, as performed at Newark, New York, and at Pleasanton, California, shows that the aforementioned characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Ridgway's Color Standards and Nomenclature:

Parentage: Seedling.
*Seed parent.*—Unnamed seedling of unknown parentage.
*Pollen parent.*—"Spartan."
Classification:
*Botanical.*—Floribunda.
*Commercial.*—Floribunda.

*Flower*

(Observations made from specimen grown outdoors at Newark, New York, in the early morning during the middle part of the month of July.)

Blooming habit: Recurrent—continuous.
Bud:
*Size.*—Large.
*Form.*—Ovoid; is not affected by wet or hot weather.
*Color.*—When sepals first divide—Testaceous, Plate 28. When petals begin to unfurl—lower half of petal Pale Lemon Yellow, Plate 4, with upper half of petal Light Coral Red, Plate 13. When half-blown: Inside of petal—Orange Pink, Plate 2, very lightly overcast with Pale Yellow-Orange, Plate 3; reverse of petals—Pale Ochraceous-Buff, Plate 15, very lightly overcast with Ochraceous-Salmon, Plate 15 and with lower half of petal overcast with Pinard-Yellow, Plate 4.

*Sepals.*—Smooth edge; curl back when petals begin to unfurl. Color: Inside—Light Lumiere Green, Plate 17; outside—Apple Green, Plate 17.
*Calyx.*—Color—Apple Green, Plate 17. Shape—apple. Size—small. Aspect—smooth. Odor when rubbed—none.
*Peduncle.*—Length—long. Aspect—rough. Strength—erect; heavy. Color—Lettuce Green, Plate 5.
*Opening.*—Opens up well; is not affected by adverse weather conditions.
Bloom:
*Size.*—Large. Average size when fully expanded—from 4½ inches to 4¾ inches.
*Borne.*—Singly and several together and in flat clusters.
*Stems.*—Long; strong.
*Form (when first open).*—Cupped and high-centered. Permanence—retains its form to the end.
*Petalage.*—Double (full but open center). Number of petals under normal conditions—from 25 to 30.
*Color.*—Center of flower—Grenadine, Plate 2. Outer petals—Cream Color, Plate 16, with edge of petals lightly overcast with Orange-Pink, Plate 2. Base of petals (aiglet)—Pale Lemon Yellow, Plate 4. Inside of petals—Pale Yellow-Orange, Plate 3, with upper half of petal lightly overcast with Orange-Pink, Plate 2 and with lower half of petal overcast with Straw-Yellow, Plate 16. Reverse of petals—Pale Ochraceous-Buff, Plate 15, with outer edge of petals overcast with Orient Pink, Plate 2 and with the lower half of petal overcast with Maize Yellow, Plate 4. General tonality from a distance—Pale Yellow-Orange, Plate 3, with upper half of petal lightly overcast with Grenadine, Plate 2.
*Discoloration.*—General tonality at end of first day—Pale Yellow-Orange, Plate 3, upper half of petal lightly overcast with Orange-Pink, Plate 2. Second day—Pale Yellow-Orange, Plate 3, with upper half of petal lightly overcast with Orange-Pink, Plate 2. Third day—Pale Yellow-Orange, Plate 3, with upper half very lightly overcast with Orange-Pink, Plate 2.
Petals:
*Texture.*—Leathery; is not affected by wet or hot weather.
*Appearance.*—Inside—satiny. Outside—shiny.
*Form.*—Oval; slightly notched.
*Arrangement.*—Imbricated (regularly arranged shingle-like).
*Petaloids in center.*—Few; large.
*Persistence.*—Drop off cleanly.
*Fragrance.*—Strong. Nature—fruity (russet apple).
*Lasting quality.*—On the plant—very long. As cut flower—very long.

*Genital organs*

Stamens, anthers: Medium size; many; regularly arranged around styles. Color—Capucine Yellow, Plate 3.
Stamens, filaments (threads): Medium length. Color—Light Cadmium, Plate 4.
Pollen: Color—Pale Yellow-Orange, Plate 3.
Styles: Bunched; uneven length; medium length; thin.
Stigmas: Color—Maize Yellow, Plate 4.
Ovaries: All enclosed in calyx.
Hips: None.
Seeds: None.

*Plant*

Form: Bush.
Growth: Vigorous; upright and bushy.

Foliage: Compound of 3 to 5 leaflets.

*Size.*—Medium.

*Quantity.*—Abundant; reaches to the ground.

*Color.*—New foliage: Upper side—Oil Yellow, Plate 5, with serrations Brazil Red, Plate 1; under side—Cosse Green, Plate 5. Old foliage: Upper side—Forest Green, Plate 17; under side—Light Elm Green, Plate 17.

*Shape.*—Oval pointed.

*Texture.*—Upper side—glossy. Under side—smooth.

*Ribs and veins.*—Ordinary.

*Edge.*—Serrated (saw toothed).

*Serration.*—Both double and single; small.

*Leaf stem.*—Color—Yellowish Oil Green, Plate 5. Under side—rough.

*Stipules.*—Medium length; smooth.

Wood:

*New wood.*—Color—Oil Yellow, Plate 5. Bark—smooth.

*Old wood.*—Color—Cress Green, Plate 31. Bark—smooth.

Thorns:

*Thorns.*—Quantity: On main stalks from base—ordinary; on laterals from stalk—ordinary. Form— narrow base; medium length; some straight and some hooked downward. Color (when young)—Old Rose, Plate 13.

*Prickles.*—Quantity: On main stalks—none; on laterals—none.

*Short needles.*—Quantity: On main stalks—none; on laterals—none.

I claim:

A new and distinct variety of rose plant of the floribunda class, substantially as herein shown and described, characterized particularly as to novelty by the unique combination of a persistent foliage which reaches to the ground all summer long, a prolific flowering habit, and a distinctive attractive and unusual general color tonality of the flowers corresponding to Pale Yellow-Orange, with the upper half of the petals being lightly overcast with Orange-Pink, and with the lower half of the petals being overcast with Straw-Yellow.

No references cited.

ABRAHAM G. STONE, *Primary Examiner.*

R. E. BAGWILL, *Assistant Examiner.*